United States Patent
Quinn et al.

(10) Patent No.: US 11,395,596 B2
(45) Date of Patent: Jul. 26, 2022

(54) CUFFLESS BLOOD PRESSURE DETERMINATION WITH A PATIENT SPECIFIC, VARIABLE CALIBRATION

(71) Applicant: Welch Allyn, Inc., Skaneateles Falls, NY (US)

(72) Inventors: David E. Quinn, Auburn, NY (US); Matthew Banet, San Diego, CA (US); Marshal Dhillon, San Diego, CA (US); Lauren Nicole Miller Hayward, La Jolla, CA (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 747 days.

(21) Appl. No.: 15/956,850

(22) Filed: Apr. 19, 2018

(65) Prior Publication Data
US 2019/0110699 A1    Apr. 18, 2019

Related U.S. Application Data (60) Provisional application No. 62/558,411, filed on Sep. 14, 2017, provisional application No. 62/594,737, filed on Dec. 5, 2017.

(51) Int. Cl.
| | | |
|---|---|---|
| A61B 5/021 | (2006.01) | |
| A61B 5/0285 | (2006.01) | |
| A61B 5/00 | (2006.01) | |

(52) U.S. Cl.
CPC ........ *A61B 5/02108* (2013.01); *A61B 5/0285* (2013.01); *A61B 5/6824* (2013.01); *A61B 5/742* (2013.01); *A61B 2560/0223* (2013.01)

(58) Field of Classification Search
CPC ..... A61B 5/021; A61B 5/0285; A61B 5/6833; A61B 5/02108; A61B 5/6824;
(Continued)

(56) References Cited

U.S. PATENT DOCUMENTS

| | | |
|---|---|---|
| 7,238,159 B2 | 7/2007 | Banet et al. |
| 7,544,168 B2 | 6/2009 | Nitzan |

(Continued)

FOREIGN PATENT DOCUMENTS

CN    2017028011 A1    2/2017

OTHER PUBLICATIONS

Physiological Monitor for Monitoring Patients Undergoing Hemodialysis Application; PERM-089-PCT.
(Continued)

*Primary Examiner* — Eric J Messersmith
(74) *Attorney, Agent, or Firm* — Lee & Hayes, P.C.

(57) ABSTRACT

A method for estimating blood pressure of a care recipient includes establishing a pre-maneuver reference value of blood pressure and a companion nonreference value of blood pressure, subjecting the care recipient to a maneuver, establishing a post-maneuver reference value of blood pressure and a companion post-manuever nonreference value of blood pressure, establishing an operational post-maneuver nonreference value of blood pressure, and adjusting the operational value as a function of the pre-maneuver and post-maneuver values. An associated apparatus includes a sensor, a processor and a memory which contains instructions. The instructions, when executed, cause the processor to estimate blood pressure as a function of a pre-maneuver reference value of blood pressure, a companion pre-maneuver nonreference value of blood pressure, a post-maneuver reference value of blood pressure, a companion post-manuever nonreference value of blood pressure, and an operational value of blood pressure based on information sensed by the sensor.

16 Claims, 12 Drawing Sheets

(58) Field of Classification Search
CPC ... A61B 5/0002; A61B 5/02125; A61B 5/742; A61B 5/022; A61B 2560/0223; A61B 5/053
See application file for complete search history.

(56) References Cited

U.S. PATENT DOCUMENTS

| | | | |
|---|---|---|---|
| 8,419,649 | B2 | 4/2013 | Banet et al. |
| 8,672,854 | B2 | 3/2014 | McCombie et al. |
| 9,585,577 | B2 | 3/2017 | Banet et al. |
| 9,901,261 | B2 | 2/2018 | McCombie et al. |
| 2010/0274143 | A1 | 10/2010 | Kim et al. |
| 2016/0353998 | A1 | 12/2016 | Lee et al. |
| 2017/0027456 | A1* | 2/2017 | Kinast ................. A61B 5/0295 |
| 2017/0172431 | A1 | 6/2017 | Kim et al. |
| 2017/0188959 | A1 | 7/2017 | Banet et al. |
| 2017/0188961 | A1 | 7/2017 | Banet et al. |
| 2018/0055389 | A1 | 3/2018 | Banet et al. |
| 2018/0303434 | A1* | 10/2018 | Selvaraj ................. A61B 5/318 |
| 2019/0343407 | A1* | 11/2019 | Huijbregts ............ A61B 5/1116 |

OTHER PUBLICATIONS

Physiological Monitor for Monitoring Patients Undergoing Hemodialysis Drawings PERM-089-PCT.

A New Cuffless Device for Measuring Blood Pressure: A Real-Life Validation Study; Journal of Medical Internet Research; ISSN 1438-8871; J Med Internet Res May 2016; 18(5): e85.; Published online May 5, 2016. doi: 10.2196/imir.5414.

A New cuff-less blood pressure monitor device—VitalSigns Technology; Sep. 2, 2016 by jL juang.

Continuous noninvasive arterial pressure—Wikipedia—Jul. 27, 2017.

Journal of the American Socity of Hypertension 4(6) (2010)284-289; Research Article; The relation between blood pressure changes induced by passive leg raising and arterial stiffness; Haroon Kamran, MD et al.; Division of Cardiovascular Medicine, State University of New York Downstate Medical Center, Brooklyn, New York, USA; Manuscript received Jun. 25, 2010 and accepted Sep. 5, 2010.

* cited by examiner

PRE-MANEUVER

POST-MANEUVER

FIG. 10

PRE-MANEUVER

POST-MANEUVER

FIG. 11

PRE-MANEUVER  POST-MANEUVER

*FIG. 12*

PRE-MANEUVER  POST-MANEUVER

CUFFLESS BLOOD PRESSURE DETERMINATION WITH A PATIENT SPECIFIC, VARIABLE CALIBRATION

CROSS REFERENCE

This application claims priority to U.S. Provisional Applications 62/558,411 filed on Sep. 9, 2017 and 62/594,737 filed on Dec. 5, 2017, the contents of both of which are incorporated herein by reference.

TECHNICAL FIELD

The subject matter described herein relates to a cuffless, noninvasive method and system for determining the blood pressure of a care recipient. In particular, the method and associated system employ a nonconstant adjustment to the actual cuffless reading to produce a result whose accuracy exceeds that of conventional cuffless techniques and systems.

BACKGROUND

The blood pressure of a care recipient, such as a physician's patient, may be determined in a number of ways. One way is to use a catheter connected to a pressure sensor. The catheter is inserted into one of the patient's arteries thereby allowing the patient's blood pressure to be measured directly. Direct arterial measurement is highly accurate and provides a continuous measurement. However the direct arterial approach is invasive and potentially hazardous. Because of the accuracy of the arterial method, blood pressure determinations made by that method are referred to herein as measurements. By contrast, determinations of blood pressure by non-arterial techniques may be more correctly described as estimates.

Another way to determine a care recipient's blood pressure is to use a commonplace cuffed-based system which employs an inflatable cuff wrapped around the patient's arm. The cuff is inflated to collapse the artery extending through the patient's arm, thereby stopping the flow of blood. The cuff is then slowly deflated, progressively reducing pressure on the artery and allowing blood flow to become re-established. As blood flow becomes re-established a caregiver or an automated subsystem checks for signals associated with systole and diastole and equates the corresponding cuff pressures to the patient's systolic and diastolic blood pressure values. Cuff-based systems are noninvasive but, unlike the direct arterial method, do not provide continuous information. Instead, they provide estimates of only systolic and diastolic pressure at essentially a single point in time. If the systolic and diastolic estimates are required at another time, the entire process must be repeated.

Another way to determine blood pressure is by way of a noninvasive cuffless method. Unless noted otherwise, the remainder of this specification uses "cuffless" to mean "noninvasive cuffless". Cuffless methods include impedance cardiography and techniques that rely on pulse transit time (PTT) and other cardiac parameters. The physical elements of a cuffless system may include an adhesive patch that can be applied to the patient's skin. An example patch includes one or more on-board sensors, an on-board memory, an on-board processor, and an on-board communications module or other component for communicating with an off-board destination. Once the patch is affixed to a patient's skin, the sensors sense physiological signals which correspond to parameters useful for estimating blood pressure. The processor uses these parameter signals to produce an estimate of the patient's blood pressure.

Cuffless systems, like cuff-based systems, have the advantage of being noninvasive. Cuffless systems have the further advantage of being able to provide continuous readings of the patient's blood pressure. However the estimates produced by cuffless systems can be less accurate than those produced by cuff-based systems and methods. The inaccuracy manifests itself in two ways.

First, for any cuff-based value of blood pressure, the cuffless value, taken at an equivalent time, will usually be different. (The notion of an "equivalent time" is described below.) Moreover the difference is not the same for different patients. For example if the cuff-based reading is 140 mmHg for each of two different patients, the time-equivalent cuffless reading might be 130 for one of the patients and 145 for the other. The difference (-10 or +5 in the foregoing examples) is referred to herein as a static offset.

Second, the sensor signals used by cuffless systems do not change in response to a change in blood pressure in a universally predictable and consistent way for all members of a population. For example a first patient whose cufflessly estimated systolic blood pressure increases by 20% (e.g. from 130 mmHg at 10:00 am to 156 mmHg at 1:00 pm) may have experienced an actual change of 20%. A second patient whose cufflessly estimated systolic pressure changes by 20% may have experienced only a 5% change in his actual systolic pressure. In other words, changes in a patient's blood pressure as determined by the cuffless method are specific to that patient, or at least cannot be relied upon as an accurate representation of how a different patient's blood pressure readings would change when determined by the same cuffless method.

In order to compensate for the static offset, a caregiver carries out a patient specific calibration of the cuffless system before relying on its readings. Calibration involves determining the patient's blood pressure with the cuffless system and with a reference system (e.g. cuff-based) at equivalent times (referred to as the calibration time or calibration point) and informing the cuffless system of the reading from the reference system. The reference system is then removed from the patient (or simply disregarded) and all subsequent readings are taken from the cuffless system. The processor of the cuffless system estimates the patient's blood pressure as:

$$P_{CUFFLESS,EST}(t) = P_{REFERENCE} + [P_{CUFFLESS}(t) - P_{CUFFLESS}(t_{reference})] \quad (1)$$

where:
- $P_{CUFFLESS,EST}(t)$ is the estimate made by the cuffless system for any time t;
- $P_{REFERENCE}$ is the reference pressure, i.e. the pressure determined by the cuff-based system at the calibration point;
- $t_{reference}$ is the calibration time, i.e. the time at which the reference pressure was determined;
- $P_{CUFFLESS}(t)$ is the pressure reported by the cuffless system at any time t; and
- $P_{CUFFLESS}(t_{reference})$ is the pressure determined by the cuffless system at calibration time $t_{reference}$.

In other words, the estimated cuffless pressure is the reference pressure plus the amount by which the pressure determined by the cuffless system has changed relative to its value at the time the reference reading was taken. The term $[P_{CUFFLESS}(t) - P_{CUFFLESS}(t_{reference})]$ may be thought of as the change in blood pressure determined by the cuffless system between time $t_{reference}$ and time t. That change is added to the reference pressure determined at $t_{reference}$ to obtain the estimate $P_{CUFFLESS,EST}(t)$. When $t=t_{reference}$, $P_{CUFFLESS,EST}(t)=P_{REFERENCE}$.

Equation (2) below is equivalent to equation (1).

$$P_{CUFFLESS,EST}(t)=P_{CUFFLESS}(t)+[P_{REFERENCE}-P_{CUFFLESS}(t_{reference})]. \quad (2)$$

In equation (2) the term $[P_{REFERENCE}-P_{CUFFLESS}(t_{reference})]$ can be thought of as a constant bias which must be applied to the cuffless pressure readings, $P_{CUFFLESS}(t)$, in order to adjust those readings to values that are more representative of the readings that would have been obtained by using the reference system.

In practice, $P_{REFERENCE}$ and $P_{CUFFLESS}(t_{reference})$ need not be established at exactly the same point in time provided they are established at equivalent times within a time interval. Equivalent times are times at which the two pressures can be considered to be companions of each other. The pressures are companions of each other if they are determined within a time interval during which the state of the care recipient remained constant with respect to his blood pressure, i.e. did not change in a way that would, in the judgement of a knowledgeable caregiver, materially affect his blood pressure. For example if the patient had been relaxed and sitting in a chair when the reference reading was taken, and remained in the relaxed and seated state for a cuffless reading taken two minutes later, the two times are equivalent times and the two readings may be viewed as companion readings despite not having been taken at exactly the same time. By contrast, if the patient had undergone a change of state (e.g. became agitated, changed posture from seated to standing, or moved around between the two readings) the change in the patient's state might cause those readings to not qualify as companions. Accordingly, $t_{reference}$ as used in this specification can refer to either a single time at which both the reference and cuffless pressures are established or to distinct times within a time interval that satisfies the above criterion of a constant state of the patient.

The above described calibration accounts for any constant bias between the cuffless system and the reference system at the calibration point. Equations (1) and (2) assume that the static offset applies at all future times irrespective of changes in the patient's blood pressure. However as already noted, the sensor signals used by cuffless systems do not change in response to a change in blood pressure over time in a universally predictable and consistent way for all members of a population. Therefore, although the above described calibration adequately accounts for inaccuracy of the cuffless system at $t_{reference}$, it may be less effective when the patient's blood pressure determined by the cuffless system at some later time deviates from $P_{CUFFLESS}(t_{reference})$.

What is needed is a cuffless system whose sensor based values of estimated blood pressure can be adjusted in a way specific to a patient in order to compensate for the above mentioned lack of consistency and predictability as the patient's blood pressure changes.

SUMMARY

A method for estimating blood pressure of a care recipient includes establishing a pre-maneuver reference value of blood pressure and a companion nonreference value of blood pressure, subjecting the care recipient to a maneuver that changes his actual blood pressure, establishing a post-maneuver reference value of blood pressure and a companion post-maneuver nonreference value of blood pressure, establishing an operational post-maneuver nonreference value of blood pressure, and adjusting the operational value as a function of the pre-maneuver and post-maneuver values.

An associated apparatus includes a sensor, a processor and a memory which contains instructions. The instructions, when executed, cause the processor to estimate blood pressure as a function of a pre-maneuver reference value of blood pressure, a companion pre-maneuver nonreference value of blood pressure, a post-maneuver reference value of blood pressure, a companion post-maneuver nonreference value of blood pressure, and an operational value of blood pressure based on information sensed by the sensor.

BRIEF DESCRIPTION OF THE DRAWINGS

The foregoing and other features of the various embodiments of the method and system for blood pressure determination described herein will become more apparent from the following detailed description and the accompanying drawings in which.

DETAILED DESCRIPTION

Figure 1:
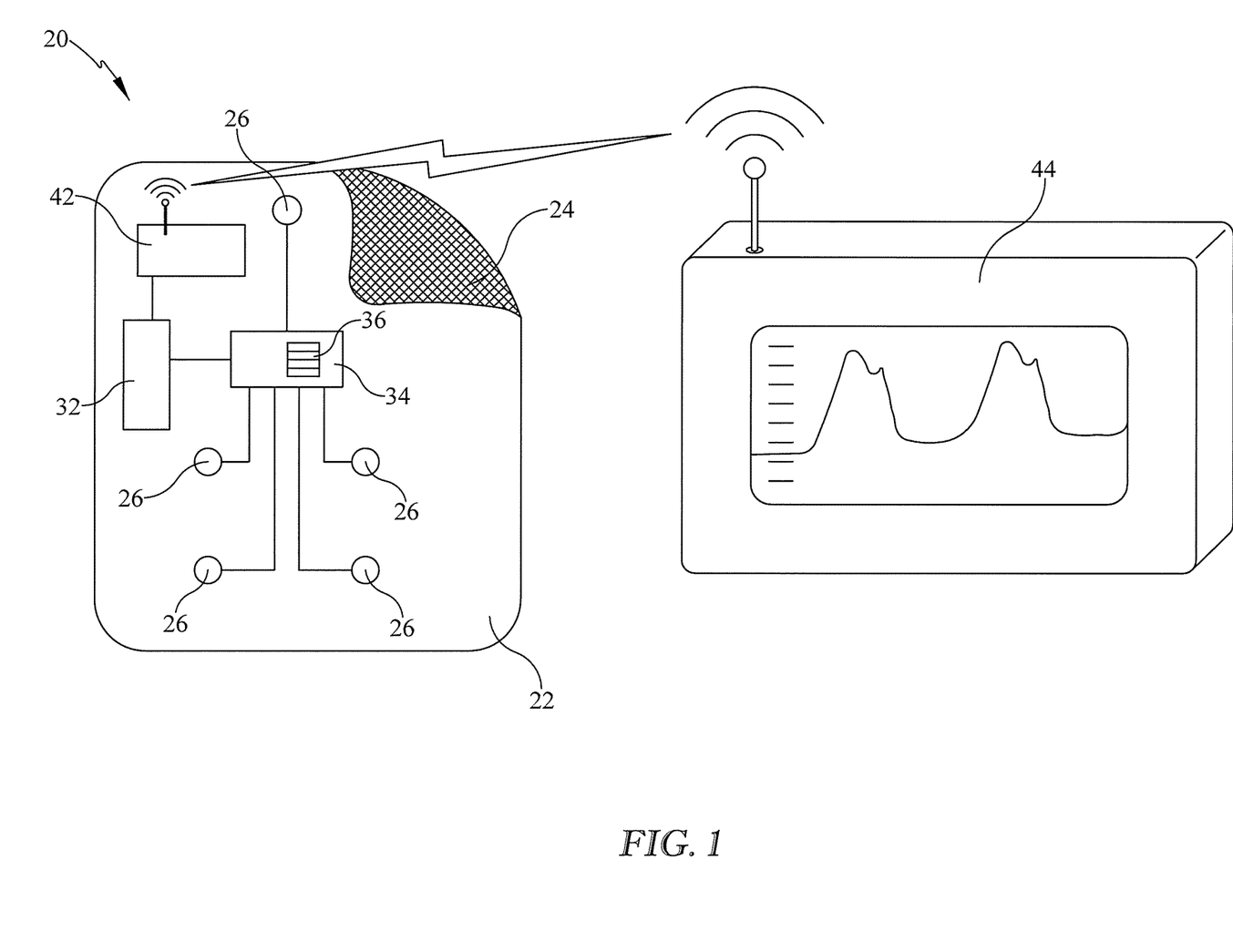
FIG. 1 is a schematic diagram of a cuffless blood pressure patch and a display module for displaying the blood pressure determined by the patch.

Referring to FIG. 1, a cuffless blood pressure monitoring patch 20 includes a substrate 22, an adhesive 24 distributed over one side of the substrate, on-board sensors 26, an on-board processor 32, and an on-board memory 34 containing instructions 36 which are executable by the processor. An on-board communications module, illustrated as a wireless module 42, facilitates communication between the patch and an off-board destination such as a display module 44 that displays blood pressure in units such as millimeters of mercury. Processor 32 and memory 34 may be off-board components rather than being on-board the patch.

During operation, and with the patch adhered to a patient, each sensor senses a physiological signal which corresponds to a parameter useful for determining blood pressure. Operating under instructions 36, the processor calculates an estimate of the patient's blood pressure from those parameter signals. Those skilled in the art will recognize that instructions 36 may be expressed in terms of parameters related to blood pressure rather than in terms of blood pressure itself. However, in the interest of explanatory simplicity this specification describes the calculations and concepts in terms of blood pressure.

Figure 2:
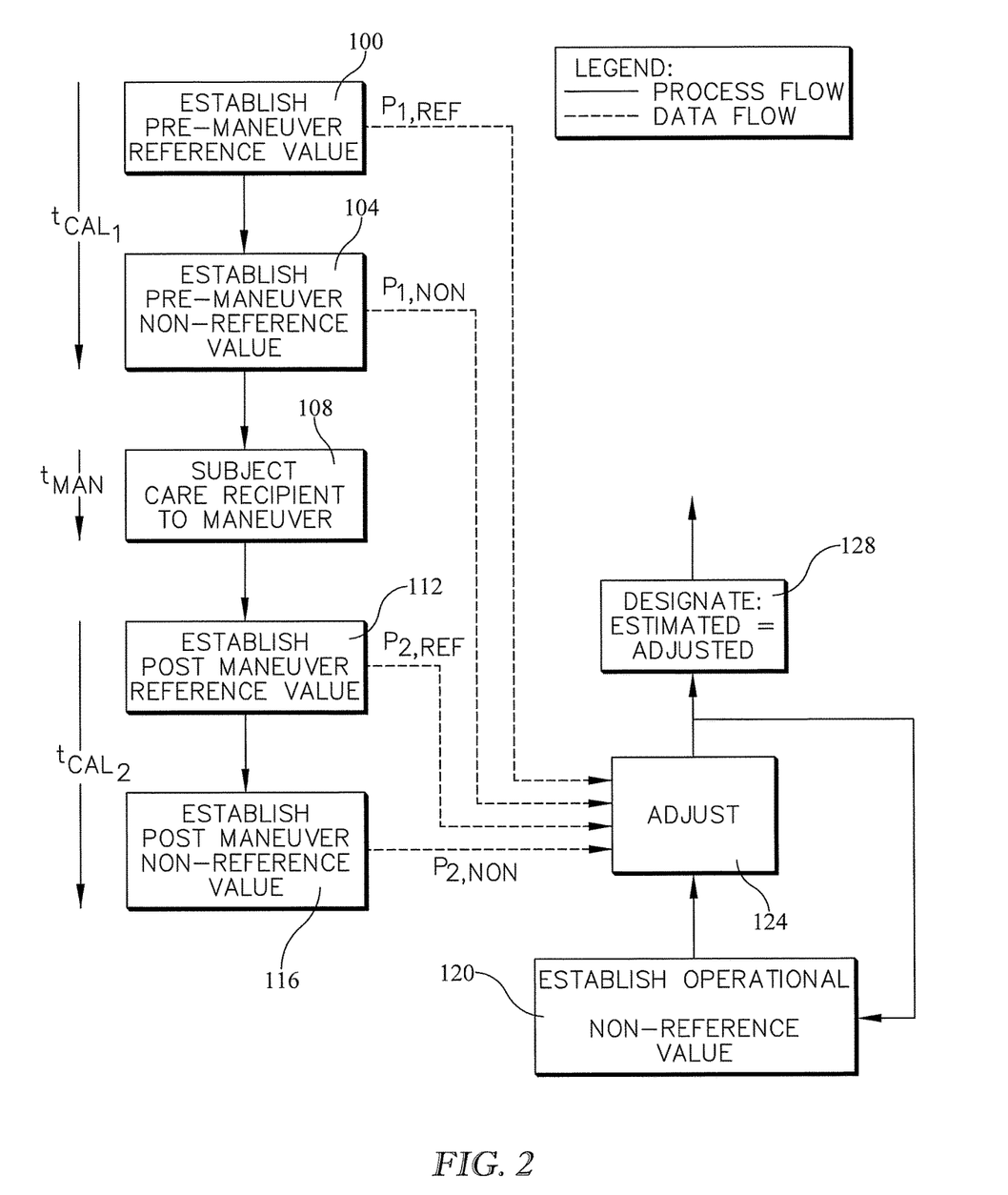
FIG. 2 is a block diagram showing the method of carrying out a cuffless blood pressure estimate as described in more detail herein.

FIG. 2 is a block diagram showing the method of carrying out a cuffless blood pressure estimate. The method accounts not only for the static offset described in the "Background" of this specification, but also for how changes in a patient's actual blood pressure over time are related to changes in the cuffless signals. As described in more detail below the method uses a reference value of the patient's blood pressure and a nonreference value of the patient's blood pressure, both of which are determined prior to the patient being subjected to a maneuver that changes the patient's actual blood pressure. The method also uses a reference value of the patient's blood pressure and a nonreference value of the patient's blood pressure, both determined subsequent to the patient having been subjected to the maneuver. In the balance of this specification, and in the claims, "patient's" may be omitted before "pressure" or "blood pressure", it being understood that the blood pressure of interest is the blood pressure of an identified patient.

At time $t_{CAL1}$, block 100 establishes a pre-maneuver reference value of blood pressure, $P_{1,REF}$. Unless stated otherwise, examples and explanations in this specification are based on using a cuff-based method as the reference.

At block 104, also at time $t_{CAL1}$, the method establishes a pre-maneuver nonreference value of blood pressure, $P_{1,NON}$. The nonreference value is based on a cuffless technique. One example of a cuffless technique is one that relies on one or more cardiac parameters such as pulse transit time, impedance measurements, and heart sounds.

Blocks 100 and 104 are a pre-maneuver calibration step carried out at pre-maneuver calibration time $t_{CAL1}$. The pre-maneuver calibration step corresponds to the single calibration described in the "Background" section of this application. That is:

$P_{1,REF}$ corresponds to $P_{REFERENCE}$;
$P_{1,NON}$ corresponds to $P_{CUFFLESS}(t_{reference})$; and
$t_{CAL1}$ corresponds to $t_{reference}$.

The pre-maneuver reference and nonreference values need not be established at exactly the same time, provided they are companion values established at equivalent times as already described above in connection with determining a static offset at $t_{reference}$. Accordingly, $t_{CAL1}$ as used in this specification can refer to either a single time at which both $P_{1,REF}$ and $P_{1,NON}$ are established or to distinct times within a time interval that satisfies the above criterion of a constant state of the patient. In addition, the readings at blocks 100 and 104 can be taken in the opposite order of that shown.

At block 108 the patient is subjected to a maneuver, examples of which are described below. The phrase "is subjected to" includes maneuvers in which the patient is passive and the maneuver is the result of an external influence acting on the patient (passive maneuvers), maneuvers that are undertaken by the patient himself without the action of an external influence (active maneuvers), and maneuvers that are partly passive and partly active. The maneuver is one which will cause the patient's actual blood pressure to change. The time at which the maneuver takes place is $t_{MAN}$. Because the maneuver is not instantaneous, $t_{MAN}$ may be considered to be an interval of time corresponding to the conduct of the maneuver rather than a discrete point in time.

The method then proceeds to block 112 where, at time $t_{CAL2}$, it establishes a post-maneuver reference value of blood pressure $P_{2,REF}$. Time $t_{CAL2}$ is later than time $t_{CAL1}$ and is a time after which any blood pressure transients associated with the maneuver have dissipated.

After the reading at block 112 has been obtained, the equipment used to establish reference values $P_{1,REF}$ and $P_{2,REF}$ is no longer needed, and so can be removed from the patient (or its readings disregarded).

At block 116, also at time $t_{CAL2}$, the method determines a post-maneuver nonreference value of blood pressure, $P_{2,NON}$. The nonreference value is based on a cuffless technique.

Blocks 112 and 116 are a post-maneuver calibration step carried out at post-maneuver calibration time $t_{CAL2}$. Neither the maneuver nor the post-maneuver calibration step have a counterpart in the above described prior art method.

The post-maneuver reference and nonreference values need not be established at exactly the same time, provided they are companion values established at equivalent times as already described above in connection with determining the pre-maneuver values at $t_{CAL1}$. Accordingly, $t_{CAL2}$ as used in this specification can refer to either a single time at which both $P_{2,REF}$ and $P_{2,NON}$ are established or to distinct times within a time interval that satisfies the above criterion of a constant state of the patient. In addition, the readings at blocks 112 and 116 can be taken in the opposite order of that shown.

At block 120 the method establishes an operational value of blood pressure $P_{NON}(t)$ (equivalent to $P_{CUFFLESS}(t)$) based on the parameter signals sensed by sensors 26. The value established at block 120 is referred to as "operational" because it forms the basis for determining the blood pressure value to be communicated to display module 44 for continuous use by the patient's caregivers. The operational value may be established with the same equipment used to establish the pre-maneuver and post-maneuver nonreference values at blocks 104 and 116.

At block 124 the method adjusts the operational value as a function of the pre-maneuver reference value, the pre-maneuver nonreference value, the post-maneuver reference value, and the post-maneuver nonreference value. At block 128 the method designates the adjusted value as the estimated blood pressure of the patient. The communications module 42 (FIG. 1) conveys this estimated blood pressure value to a destination such as display module 44.

After block 124 the method also follows a path back to block 120 and continues to loop through blocks 120 and 124. As a result the operational value is periodically updated, and the updated value is adjusted by the functional relationship determined from the pre-maneuver and post-maneuver reference and nonreference values. The operations at blocks 120, 124, and 128 may be repeated at a low frequency or may be repeated at a high enough frequency that the output of block 128 approximates a continuous, analogue output.

Figure 3:
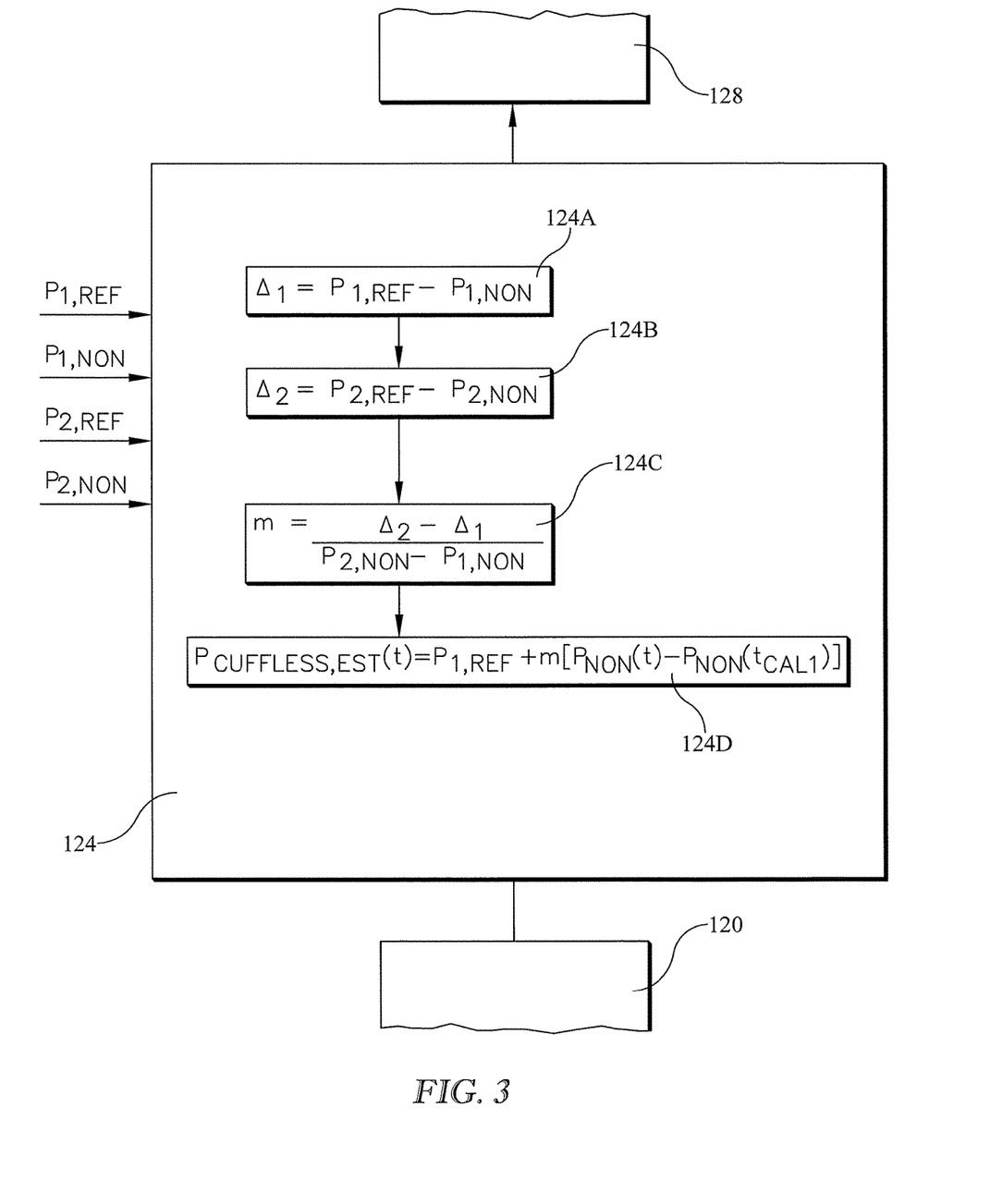
FIG. 3 shows the adjustment block of FIG. 2 in more detail.

FIG. 3 shows the adjustment of block 124 in more detail. Block 124A calculates $\Delta_1$, the difference between pre-maneuver reference pressure $P_{1,REF}$ (e.g. a cuff-based reading) and pre-maneuver nonreference pressure $P_{1,NON}$ (the cuffless reading). $\Delta_1$ is the previously described static offset.

Block 1243 calculates $\Delta_2$, the difference between post-maneuver reference pressure $P_{2,PEF}$ and post-maneuver nonreference pressure $P_{2,NON}$. $\Delta_2$ may be referred to as a post-maneuver static offset, but, unlike the premaneuver static offset $\Delta_1$, has no counterpart in the conventional calibration described in the "Background" section of this specification.

Block 124C calculates m, the extent to which the static offset $\Delta_1$ changes in response to changes in blood pressure indicated by the cuffless system.

Block 124D calculates an estimate of cuffless blood pressure, $P_{CUFFLESS,EST}$ at any time t as a function of 1) $P_{1,REF}$ the pre-maneuver reading obtained from the reference system at the calibration time $t_{CAL1}$, 2) slope m, 3) $P_{NON}(t)$, the readings at any time t obtained from the cuffless (nonreference) system and 4) $P_{NON}(t_{CAL1})$, (or, equivalently, $P_{1,NON}$) the cuffless pressure determined at the pre-maneuver calibration point. The relationship used at block 124D is reproduced below:

$$P_{CUFFLESS,EST}(t)=P_{1,REF}+m[P_{NON}(t)-P_{NON}(t_{CAL1})]. \quad (3)$$

In view of the fact that $P_{NON}(t)$ is the same as $P_{CUFFLESS}(t)$, equation (3) can also be expressed as:

$$P_{CUFFLESS,EST}(t)=P_{1,REF}+m[P_{CUFFLESS}(t)-P_{CUFFLESS}(t_{CAL1})]. \quad (4)$$

The subtrahend in the above equations is the same as $P_{1,NON}$.

Figure 4:
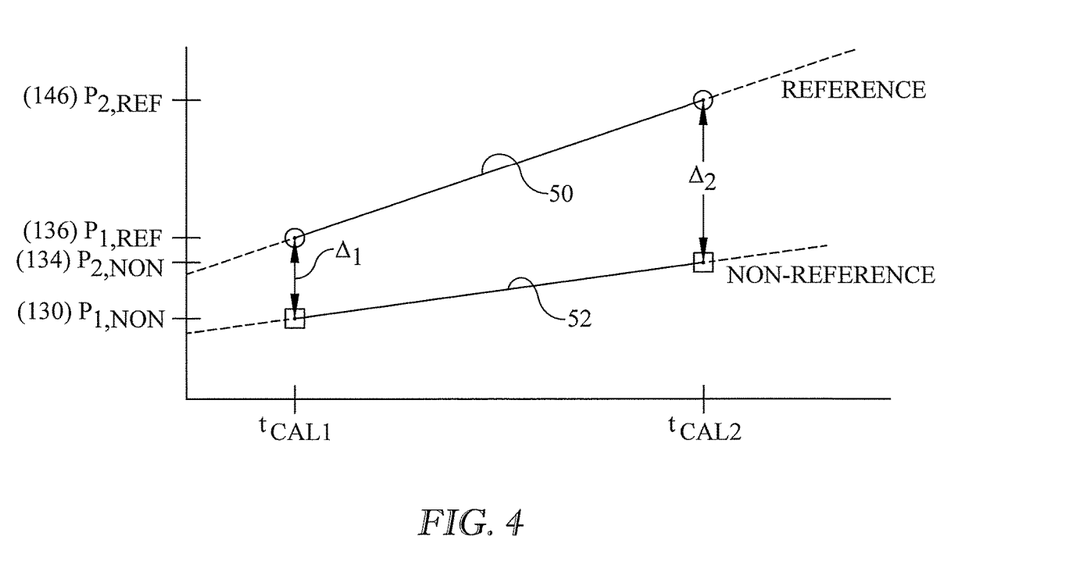
FIG. 4 is a graph showing a prophetic example of pre-maneuver and post-maneuver reference and nonreference blood pressure values used in the method disclosed herein with a linear relationship extending between and extrapolated beyond the displayed values.

FIG. 4 is a graph showing a numerical example of pre-maneuver and post-maneuver reference and nonreference blood pressure values. The values are illustrative only, not actual data. A linear reference pressure relationship 50 is shown extending between and extrapolated beyond the reference readings (circular symbols). A linear nonreference pressure relationship 52 is shown extending between and extrapolated beyond the nonreference readings (square symbols). A similar graph of the reference and nonreference relationships based on actual readings could have different slopes and y-axis intercepts. The difference $\Delta_1$ between the pre-maneuver blood pressure readings, is referred to as the pre-maneuver static offset and corresponds to the prior art static offset previously described in the context of determining a constant bias. The difference $\Delta_2$ between the post-maneuver blood pressure readings is referred to as the post-maneuver static offset and has no counterpart in the prior art method.

Figure 5:
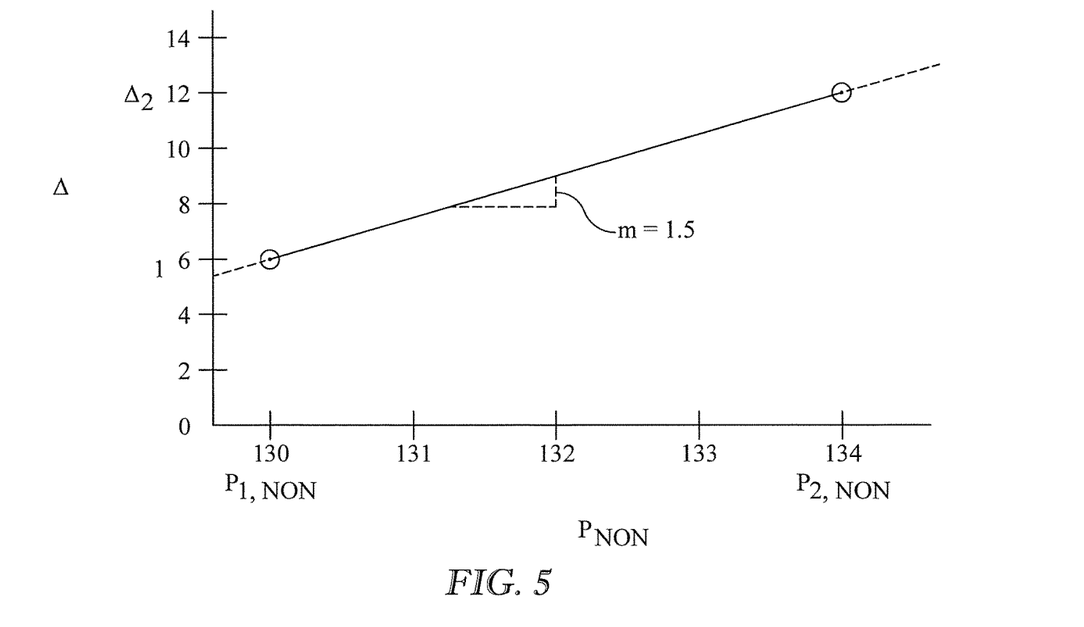
FIG. 5 is a graph showing pre-maneuver and post-maneuver static offsets between the reference and nonreference graphs of FIG. 3 as a function of the nonreference values of blood pressure.

FIG. 5 is a graph showing the pre-maneuver and post-maneuver static offsets as a function of the nonreference values of blood pressure. The functional relationship, which is defined by the depicted straight line, is a variable bias, VB. The graph reveals that when the cuffless system reads 130, that value should be adjusted by +6, and that when the cuffless system reading differs from 130, the adjustment should also be different. Specifically, for every 1.0 mm Hg that the cuffless value differs from 130, the adjustment should change by 1.5 mm Hg, as indicated by the slope of the graph of FIG. 5.

Figure 6:
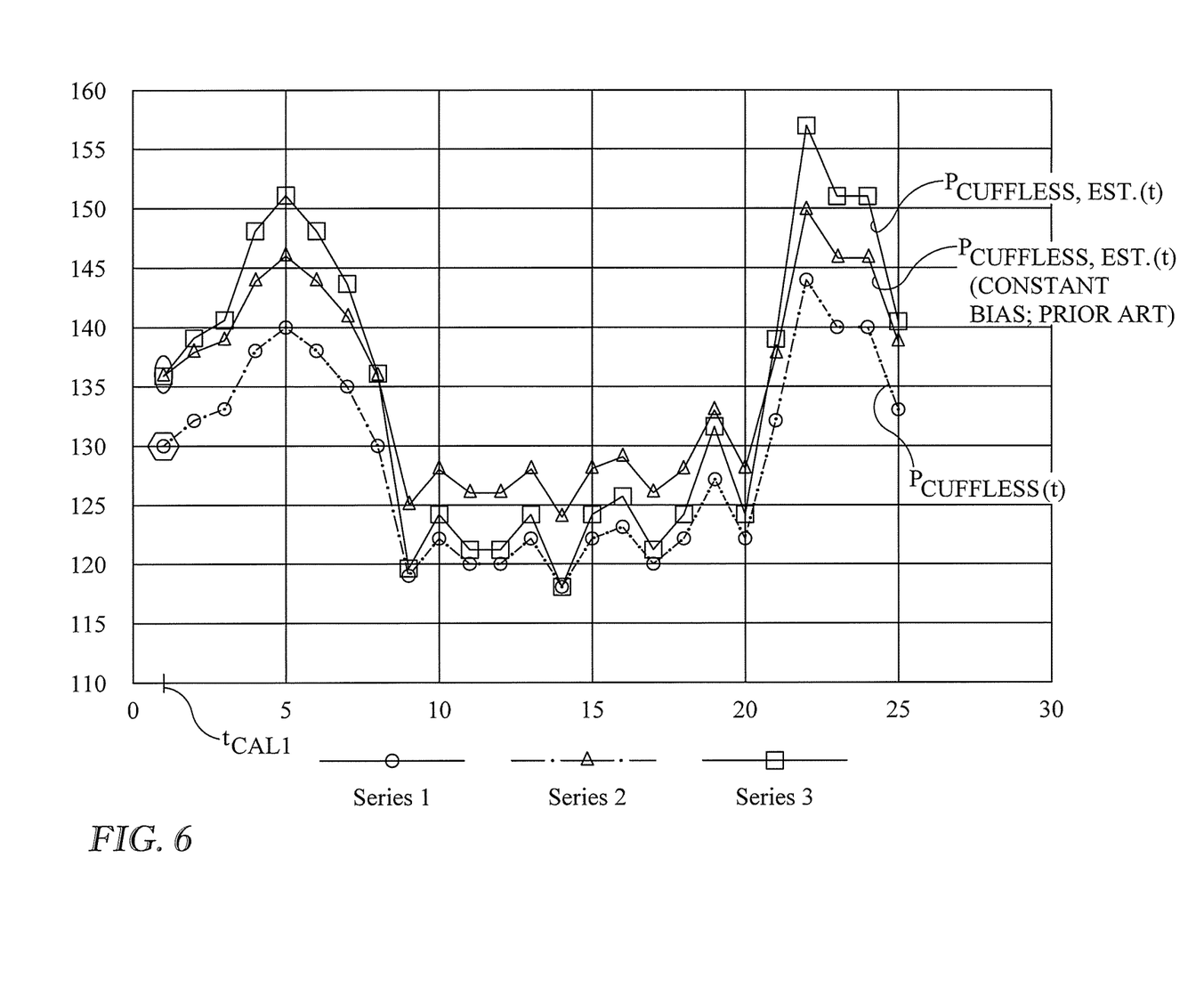
FIG. 6 is a graph of the prophetic numerical example showing twenty five blood pressure readings according to the method described herein and also showing, for comparison, the results of a prior art method.

Table 1 below and FIG. 6 show twenty five example blood pressure values according to the method described herein. The table and graph also show, for comparison, the results of a constant bias prior art method. The circular symbols connected by the dashed-dot line are the unadjusted cuffless blood pressure readings $P_{CUFFLESS}(t)$ taken at twenty five different points in time. The hexagonal border around the leftmost (first) reading indicates that $P_{CUFFLESS}(1)-P_{CUFFLESS}(t_{CAL1})=P_{1,NON}=P_{NON}(t_{CAL1})$.

The triangular symbols connected by the dashed line are the values of $P_{CUFFLESS,EST}$ that would be calculated by the prior art method in which the change in the cuffless reading relative to its value at the calibration point is added to the reference (i.e. reference) value at the calibration point (equation (1)) or, alternatively but equivalently, the unadjusted readings, $P_{CUFFLESS}(t)$, are biased by the constant calibration offset (equation (2)). In the example, the numerical value of the bias is 6. The oval border around the leftmost triangular symbol indicates that $P_{CUFFLESS,EST}(t_{CAL1})=P_{1,NON}$.

The square symbols connected by the solid line are the values of $P_{CUFFLESS,EST}(t)$ calculated based on equation (3) or (4). In this specific example, the relationship of equation (3) is $$P_{CUFFLESS,EST}(t)=136+1.5[P_{CUFFLESS}(t)-130] \quad (6)$$

where 136 is $P_{1,REF}$, 1.5 is slope m of block diagram block 124C (the slope of FIG. 4), $P_{CUFFLESS}(t)$ (or $P_{NON}(t)$) is the cuffless reading at time t, and 130 is $P_{NON}(t_{CAL1})$, the pre-maneuver nonreference value.

As is evident from FIG. 6, the difference between $P_{CUFFLESS,EST}(t)$ and $P_{CUFFLESS}(t)$ changes as a function of $P_{CUFFLESS}(t)$. In the example the difference increases by 1.5 mmHg/mmHg when $P_{CUFFLESS}(t)$ exceeds 130 and decreases by 1.5 mmHg/mmHg when $P_{CUFFLESS}(t)$ is below 130. For example at the fifth reading $P_{CUFFLESS}(t)=140$, which is a 10 mmHg. increase relative to the cuffless reading of 130 at the first reading at $t_{CAL1}$. According to the slope of FIG. 4 (m=1.5) this 10 mm Hg increase in the cuffless pressure measured by patch sensors 26 should be reflected as a 15 mmHg increase in $P_{CUFFLESS,EST}$ relative to $P_{1,REF}$. Accordingly, $P_{CUFFLESS,EST}(5)=136+15=151$.

TABLE 1

| A Reading No | B $P_{CUFFLESS}(t)$ (unadjusted) | C $P_{CUFFLESS,EST}(t)$ (Prior Art) | D $P_{CUFFLESS,EST}(t) = P_{1,REF} + m[P_{NON}(t) - P_{NON}(t_{CAL1})]$ |
|---|---|---|---|
| 1 | 130 | 136 | 136 |
| 2 | 132 | 138 | 139 |
| 3 | 133 | 139 | 140.5 |
| 4 | 138 | 144 | 148 |
| 5 | 140 | 146 | 151 |
| 6 | 138 | 144 | 148 |
| 7 | 135 | 141 | 143.5 |
| 8 | 130 | 136 | 136 |
| 9 | 119 | 125 | 119.5 |
| 10 | 122 | 128 | 124 |
| 11 | 120 | 126 | 121 |
| 12 | 120 | 126 | 121 |
| 13 | 122 | 128 | 124 |
| 14 | 118 | 124 | 118 |
| 15 | 122 | 128 | 124 |
| 16 | 123 | 129 | 125.5 |
| 17 | 120 | 126 | 121 |
| 18 | 122 | 128 | 124 |
| 19 | 127 | 133 | 131.5 |
| 20 | 122 | 128 | 124 |
| 21 | 132 | 138 | 139 |
| 22 | 144 | 150 | 157 |
| 23 | 140 | 146 | 151 |
| 24 | 140 | 146 | 151 |
| 25 | 133 | 139 | 140.5 |

Figure 7:
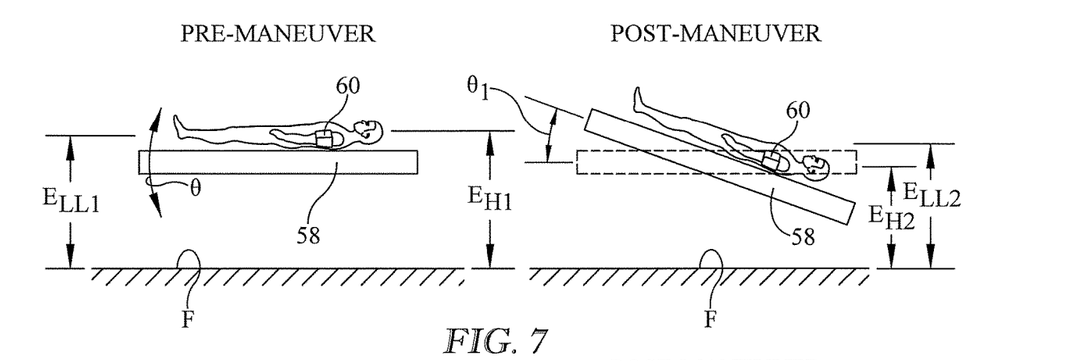
FIGS. 7-13 are schematic illustrations of example maneuvers used in the blood pressure estimating method described herein.

FIG. 7 shows one example of a maneuver carried out at block 108 of FIG. 2. The illustration shows a patient lying on a patient support element 58 of a bed. The patient support element is orientation adjustable through an angle θ. Portions of the bed between the floor F and the patient support element are not shown in order to simplify the drawing. A blood pressure cuff 60 on the patient's arm is used to establish the pre-maneuver and post-maneuver reference values of the patient's blood pressure.

In the pre-maneuver state the patient is lying with his head at a first elevation $E_{H1}$ which is not lower than the elevation $E_{LL1}$ of his lower limbs (thighs and calves) as a result of support element 58 being at an essentially horizontal orientation. In the post maneuver state the patient is lying with his head at a second elevation $E_{H2}$ which is lower than the lowest elevation $E_{LL2}$ of his lower limbs (i.e. the approximate elevation of the patient's gluteal sulcus). The maneuver is considered to be a passive maneuver because it is carried out with little or no active involvement of the patient. Instead the patient merely remains lying in the bed while its orientation is changed. The maneuver is believed to increase the patient's actual blood pressure because extra blood volume is drained to the patient's torso at the elevation of the heart, which is approximately the elevation of the blood pressure cuff. In both the pre-maneuver state and the post-maneuver state the cuff is approximately at the same elevation as the patient's heart. As a result the hydrostatic component of blood pressure is the same in both the pre-maneuver state and the post-maneuver state.

Figure 8:
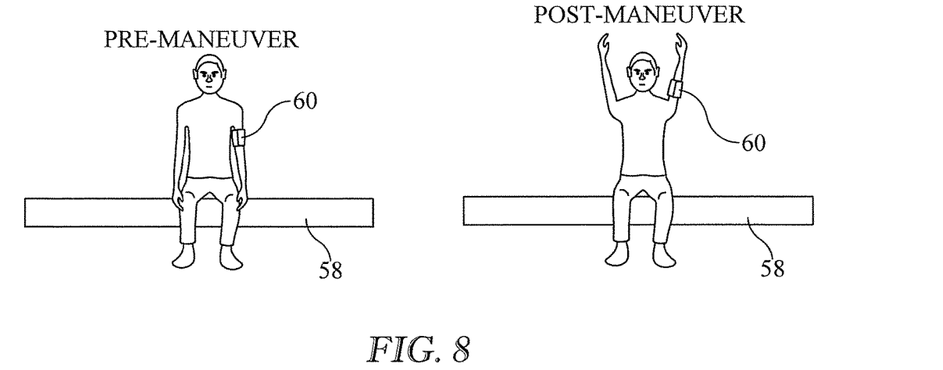

FIG. 8 shows another example maneuver. In the pre-maneuver state the patient is sitting with his arms at his sides. In the post maneuver state the patient is sitting with his arms raised above his head, and therefore above his heart. Because the maneuver elevates cuff 60 to a higher elevation than the patient's heart, the volume of blood in his arms may create a noteworthy hydrostatic effect on the pressure registered by the cuff. The hydrostatic effect will have to be factored out of the cuff-based blood pressure reading to determine the actual blood pressure. The maneuver of FIG. 8 is considered to be an active maneuver because it requires active involvement on the part of the patient.

Figure 9:
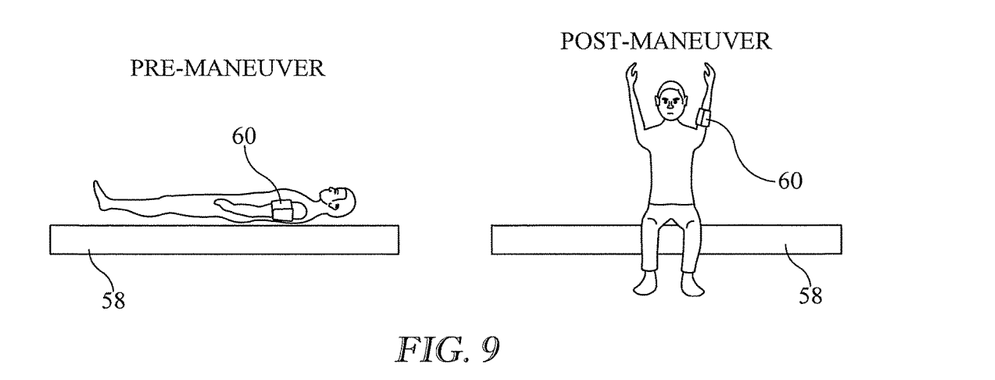

FIG. 9 shows another example maneuver. In the pre-maneuver state the patient is supine with his arms at his sides. In the post maneuver state the patient is sitting with his arms raised above his head. The maneuver is an active maneuver. As with the maneuver of FIG. 8, the hydrostatic effect will have to be accounted for.

The maneuvers of FIGS. 8-9 are specific examples of a class of maneuvers that involve transitioning the patient to a state in which the elevation of his heart is lower than the elevation of his head and arms.

Figure 10:
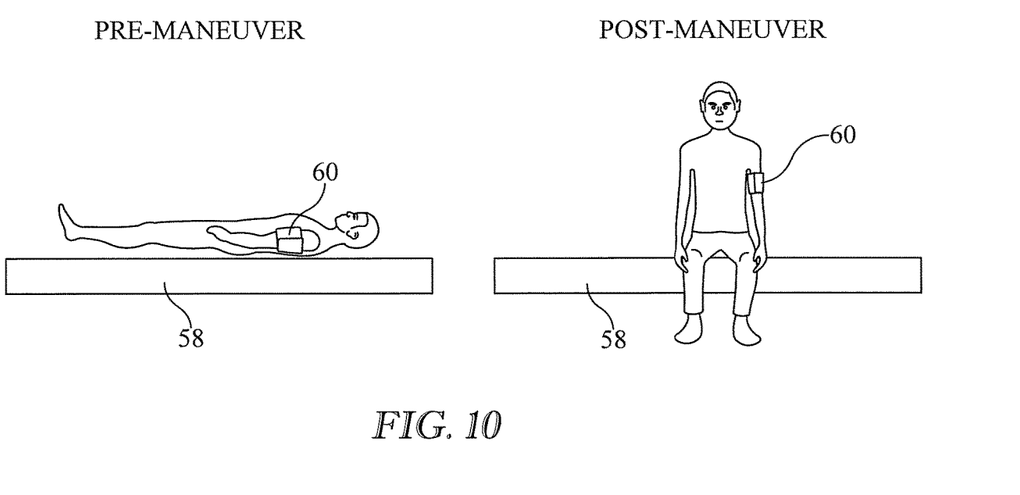
Figure 11:
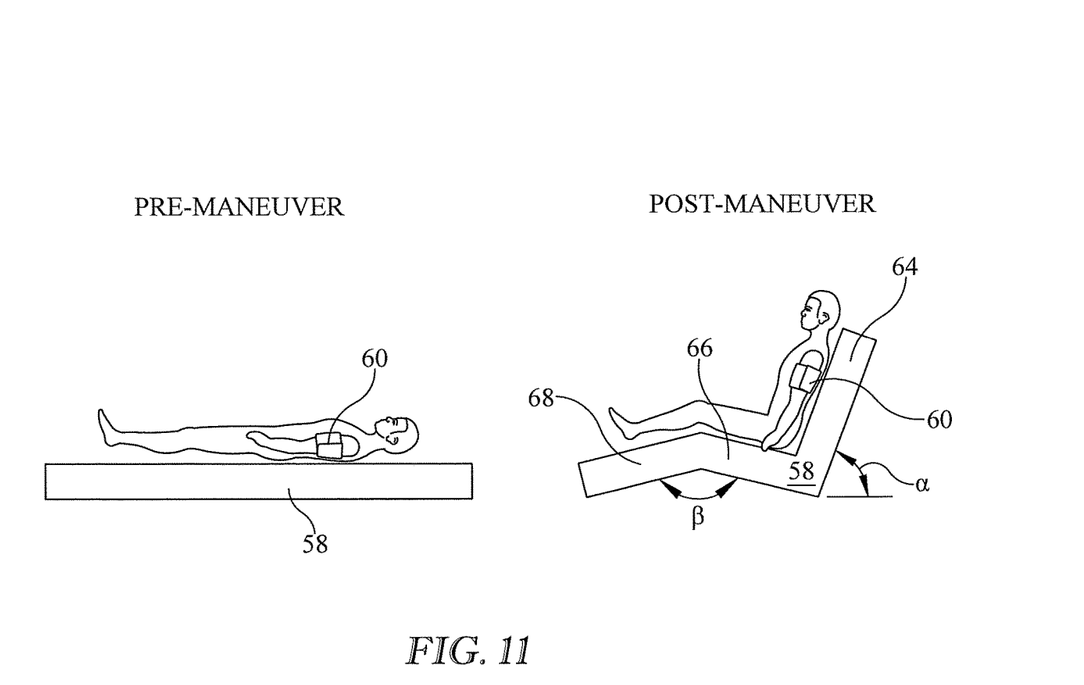

FIGS. 10-11 show two more example maneuvers. In the pre-maneuver state the patient is supine with his arms at his sides. In the post maneuver state the patient is sitting with his arms at his side. In FIG. 10 the patient has taken a seated position at the edge of the bed. The maneuver is an active maneuver. In FIG. 11 the bed has been adjusted so that its upper body section 64 is at an angle α and the thigh and calf sections 66, 68 form an angle β. The patient has been maneuvered into a seated position in which he remains completely on the bed. The maneuver is a passive maneuver.

Figure 12:
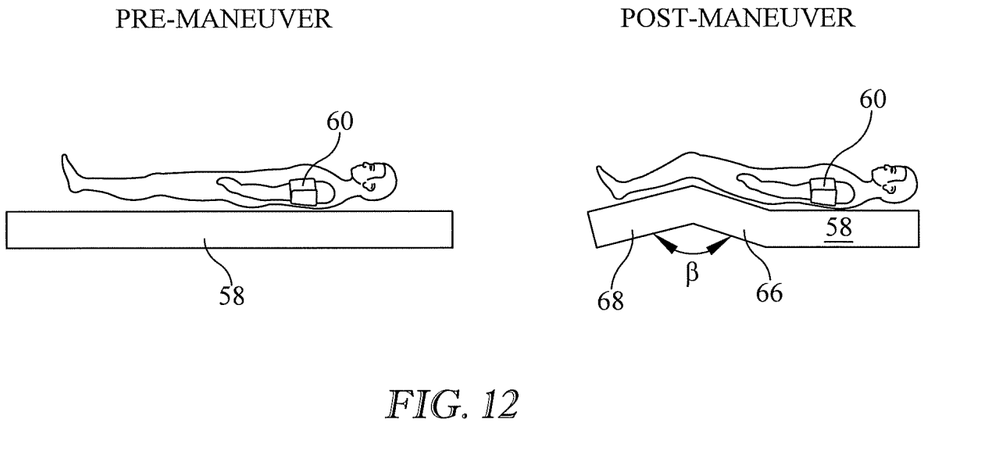

FIG. 12 shows another example maneuver. In the pre-maneuver state the patient is supine with his arms at his sides. In the post maneuver state the bed has been adjusted so that thigh and calf sections 66, 68 form an angle β but upper body section 64 remains at the pre-maneuver horizontal orientation. The maneuver is a passive maneuver.

Figure 13:
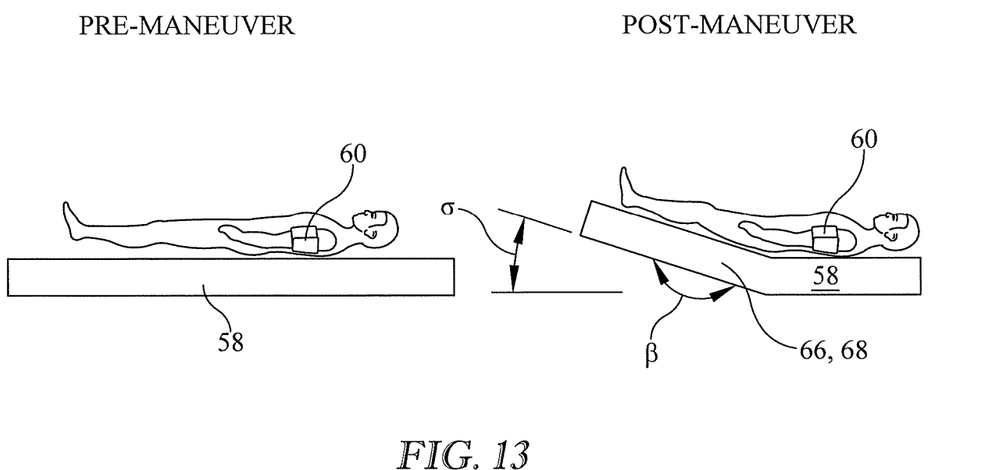

FIG. 13 shows another example maneuver. In the pre-maneuver state the patient is supine with his arms at his sides. In the post maneuver state the bed has been adjusted so that thigh and calf sections 66, 68 form an angle β of essentially 180 degrees but are inclined at an angle σ relative to the upper body section, which remains at the pre-maneuver horizontal orientation. The maneuver is a passive maneuver.

Figure 14:
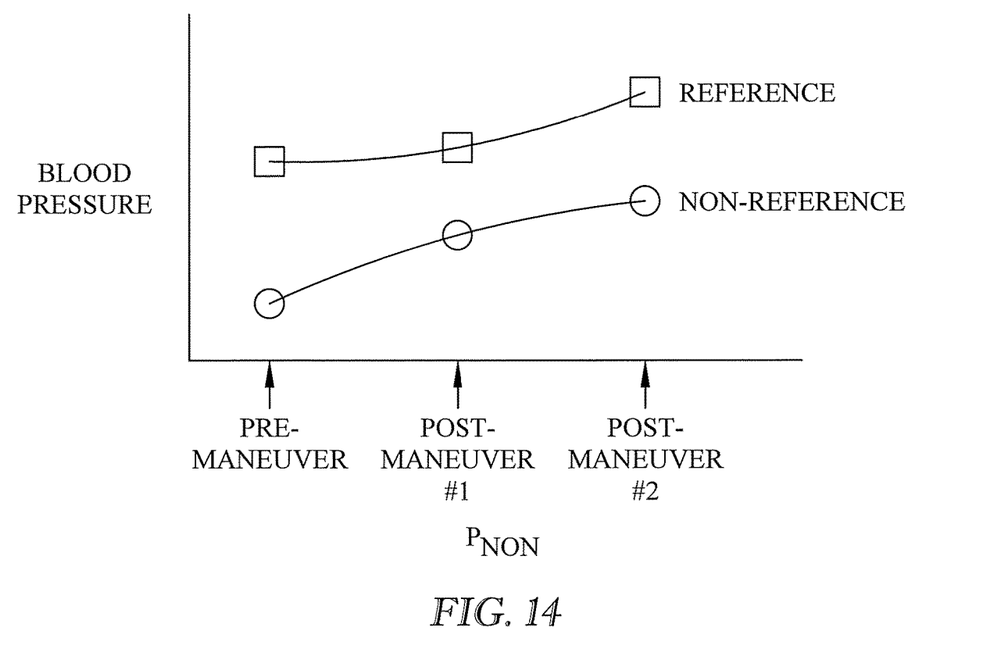
FIG. 14 is a graph showing the use of more than one maneuver in connection with the blood pressure estimating method described herein and in which the post-maneuver results are not substantially the same as each other.
Figure 15:
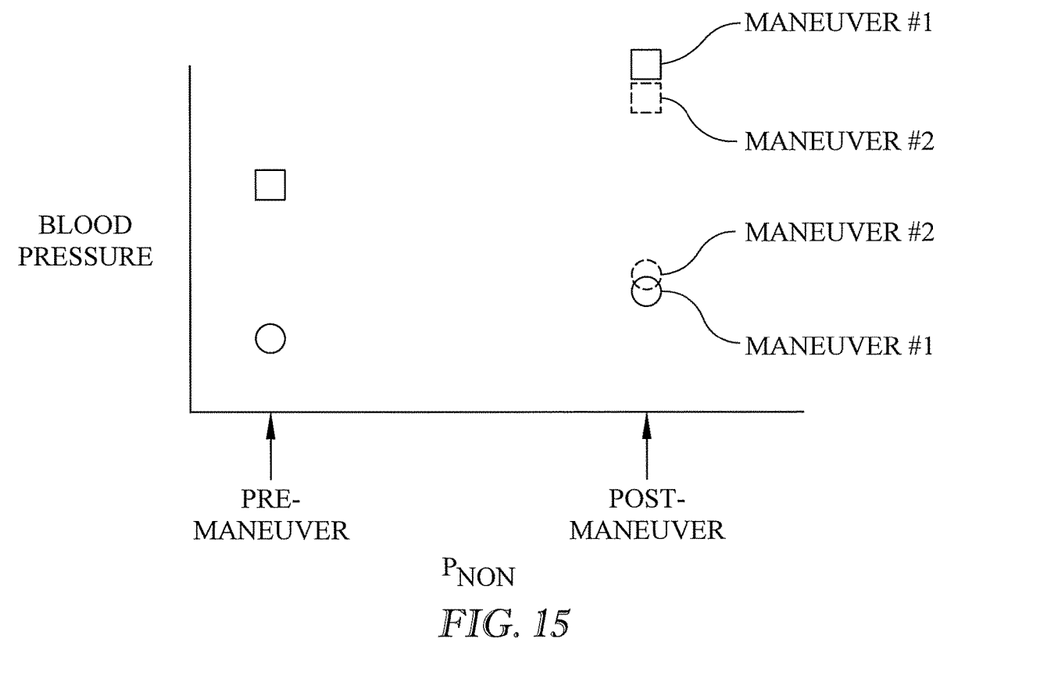
FIG. 15 is a graph similar to FIG. 14 in which the post-maneuver results are substantially the same as each other.

Each of the foregoing examples subjects the patient to a single maneuver. However multiple maneuvers can be used to establish multiple post-maneuver static offsets. In the example of FIG. 14 the additional maneuver, maneuver number 2, is one that has a materially different effect on blood pressure in comparison to the original maneuver, maneuver number 1. The additional maneuver or maneuvers can be useful for establishing a more accurate estimate of how the adjustment applied to the blood pressure of the patient under examination should change as a function of $P_{NON}$. In the example of FIG. 15 the additional maneuver is one that is not expected to have a materially different effect on blood pressure than the original maneuver. The maneuver can nevertheless be useful to validate the results obtained from the original maneuver.

The adjusting step 124 of FIGS. 2-3 may be a linear function of the pre-maneuver and post-maneuver nonreference values as seen in FIG. 5. Alternatively the function may be nonlinear as is suggested by the nonlinearly varying distance between the square and circular symbols of FIG. 14 and the nonlinear curve fits associated with those symbols.

Figure 16:
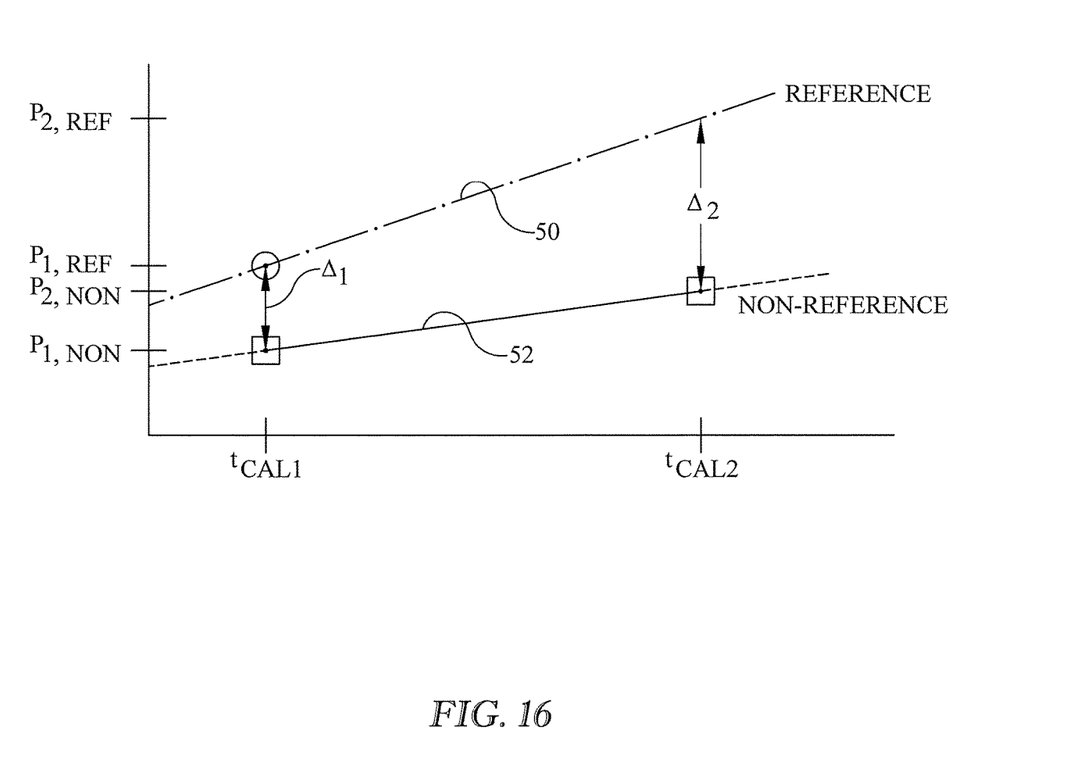
FIG. 16 is a graph similar to that of FIG. 4 illustrating the possibility of establishing the post maneuver reference value from the pre-maneuver reference value and an estimate of how the reference value changes with pressure.
Figure 17:
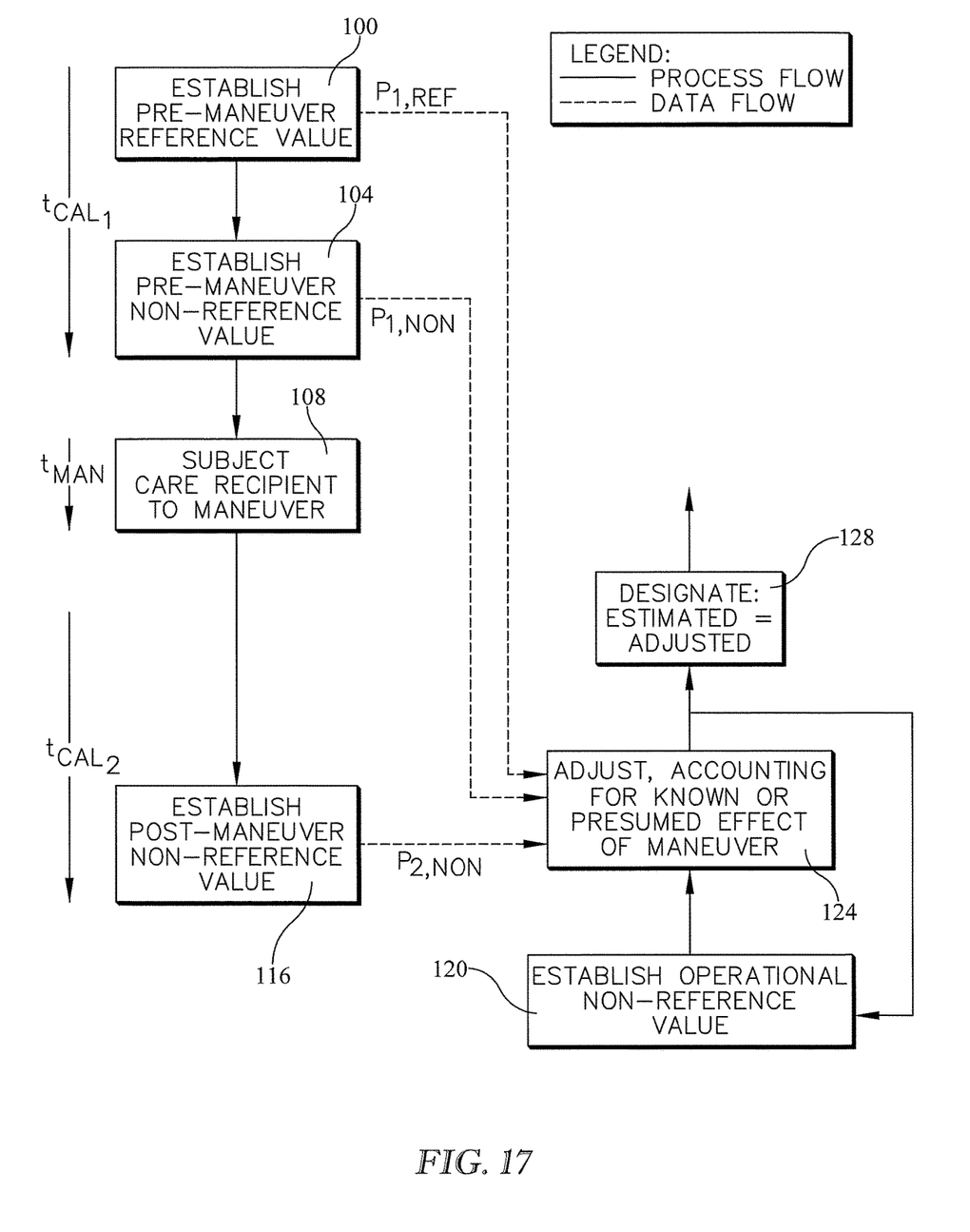
FIG. 17 is a block diagram corresponding to the method illustrated in FIG. 16.

It may also be possible to establish the post maneuver reference value from the pre-maneuver reference value and an estimate of how the reference value changes as a function of $P_{NON}$. This is indicated in FIG. 16 by the presence of only a single symbol and a dash-dot line to depict the reference relationship. The slope of the line represents a known or presumed effect of the maneuver. Otherwise, the graph of FIG. 16 is the same as that of FIG. 3. FIG. 17 is a block diagram of the method of FIG. 16. The block diagram is the same as that of FIG. 2 except that block 112 is absent, and the adjusting step of block 124 accounts for the known or presumed effect of the maneuver.

Figure 18:
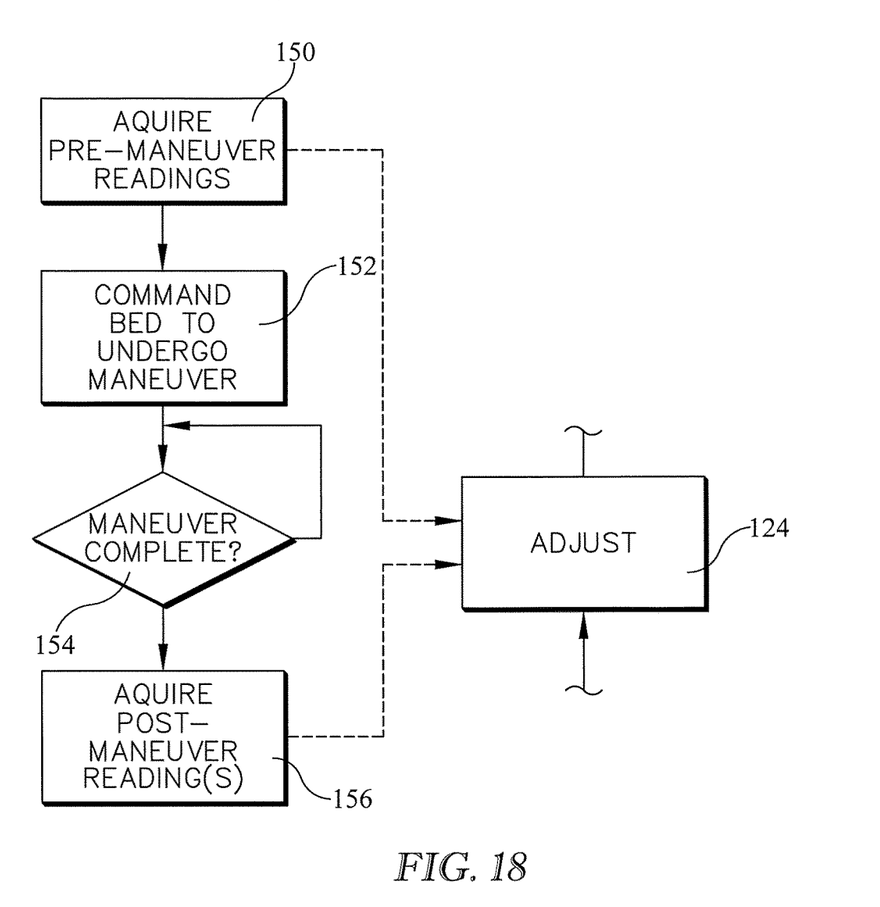
FIGS. 18-19 are a block diagram and a computer architecture schematic showing one possible way to automate the above described method described herein.
Figure 19:
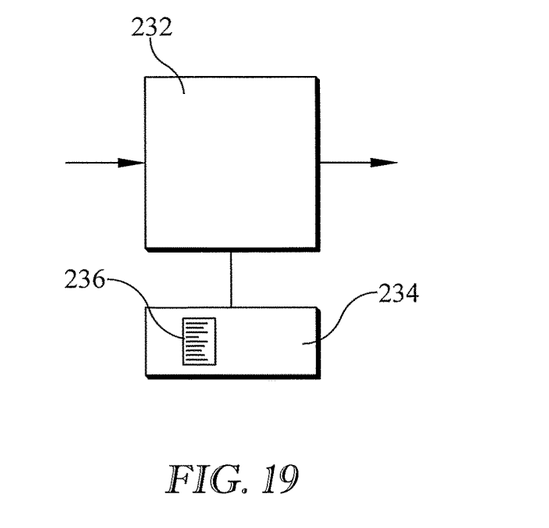

The block diagram of FIG. 18 and the computer architecture schematic of FIG. 19 show one possible way to automate the above described method. Prior to initiating the automated sequence of events shown in the diagram a caregiver sets up the reference and nonreference blood pressure monitoring systems, for example by applying a blood pressure cuff to a patient's arm and adhering a monitoring patch to the patient's skin. The caregiver also make necessary connections to the computer hardware which includes a processor 232 and a memory 234 containing instructions 236 executable by the processor.

Once the caregiver initiates the event sequence the method automatically acquires the pre-maneuver blood pressure readings at block 150. The automated sequence then proceeds to block 152 where the bed is commanded to undergo a maneuver, for example the maneuver of FIG. 7. The method then advances to block 154 where it determines if the maneuver is complete. Criteria for maneuver completeness may include determining that the bed actuators which effected the maneuver are no longer active and determining that any blood pressure transients which the maneuver may have caused have settled out. The method then proceeds to block 156 where it acquires post maneuver reference and nonreference blood pressure readings. Alternatively, the system may acquire only a post-maneuver non-reference reading as explained in connection with FIG. 16.

Although this disclosure refers to specific embodiments, it will be understood by those skilled in the art that various changes in form and detail may be made without departing from the subject matter set forth in the accompanying claims.

The invention claimed is:

1. A method for estimating blood pressure of a care recipient, comprising:
   establishing a pre-maneuver reference value of blood pressure and a companion pre-maneuver nonreference value of blood pressure;
   subjecting the care recipient to a maneuver;
   establishing a post-maneuver reference value of blood pressure and a companion post-maneuver nonreference value of blood pressure;
   establishing an operational value of blood pressure that is determined:
      based on sensed parameter signals, and
      independent of at least the pre-maneuver reference value and the post-maneuver reference value;
   adjusting the operational value as a function of the pre-maneuver reference value, the pre-maneuver nonreference value, the post-maneuver reference value, and the post-maneuver nonreference value, wherein adjusting the operational value comprises generating an adjusted value, and the pre-maneuver reference value is held constant to generate the adjusted value; and
   designating the adjusted value as the estimated blood pressure of the care recipient.

2. The method of claim 1 wherein the post-maneuver reference value is derived from the pre-maneuver reference value and a known or presumed effect of the maneuver.

3. The method of claim 1 wherein the post-maneuver reference value is based on subjecting the recipient to a single maneuver.

4. The method of claim 1 wherein the adjusting step is a linear function of the pre-maneuver and post-maneuver nonreference values.

5. The method of claim 1 wherein the pre-maneuver and post maneuver reference values are cuff-based values.

6. The method of claim 1 wherein the pre-maneuver and post-maneuver nonreference values are cuffless based values.

7. The method of claim 1 wherein the maneuver is passive with respect to the care recipient.

8. The method of claim 1 wherein the maneuver is selected from the group consisting of:
   A) transitioning the care recipient between
      a) lying with his or her head at a first elevation which is not lower than an elevation of his or her lower limbs and
      b) lying with his or her head at a second elevation which is lower than the elevation of his or her lower limbs; and
   B) transitioning the care recipient between lying with his or her arms at his or her sides and sitting with his or her arms at his or her sides.

9. The method of claim 8 wherein transitioning the care recipient between lying and sitting comprises an active maneuver in which the care recipient takes a seated position with his or her arms at his or her sides.

10. The method of claim 8 wherein transitioning the care recipient between lying and sitting comprises a passive maneuver in which the care recipient is maneuvered to a seated position with his or her arms at his or her sides.

11. The method of claim 1 wherein the pre-maneuver reference value and the post-maneuver reference value are established with the use of a cuff on one of the care recipient's arms, and the maneuver is transitioning the care recipient to a state in which the elevation of his or her heart is lower than the elevation of his or her head and arms.

12. A blood pressure monitoring system comprising:
   a sensor;
   a processor;
   a memory containing instructions which, when executed, cause the processor to:
      estimate blood pressure as a function of a pre-maneuver reference value of blood pressure, a companion pre-maneuver nonreference value of blood pressure, a post-maneuver reference value of blood pressure, a companion post-maneuver nonreference value of blood pressure, and an operational value of blood pressure, wherein the operational value of blood pressure is:
         established based on parameter signals sensed by the sensor,
         determined independent of at least the pre-maneuver reference value and the post-maneuver reference value, and
         adjusted as a function of the pre-maneuver reference value, pre-maneuver nonreference value, the post-maneuver reference value, and the post-maneuver nonreference value, and wherein:
         adjusting the operational value comprises generating an adjusted value,
         the pre-maneuver reference value is held constant to generate the adjusted value, and
         the adjusted value is designated as the estimated blood pressure.

13. The system of claim 12 wherein the instructions, when executed, cause the estimated blood pressure to be a linear function of the pre-maneuver and post-maneuver non-reference values.

14. The system of claim 12 wherein the system comprises a patch and wherein the sensor is mounted on the patch.

15. The system of claim 14 wherein the processor and/or the memory are mounted on the patch.

16. The system of claim 12 comprising a patient support element and wherein the instructions, when executed, cause the patient support element to carry out the maneuver.

* * * * *